United States Patent [19]
Hoppe et al.

[11] Patent Number: 5,968,778
[45] Date of Patent: Oct. 19, 1999

[54] PDGF-AB, PREPARATION PROCESS AND PHARMACEUTICALS CONTAINING THEM

[75] Inventors: Jurgen Hoppe, Koellikerstr. 2, 8700 Wurzburg; Herbert Weich, Freiburg, both of Germany

[73] Assignee: Jurgen Hoppe, Germany

[21] Appl. No.: 08/804,953

[22] PCT Filed: Jan. 11, 1990

[86] PCT No.: PCT/EP90/00063

§ 371 Date: Aug. 7, 1991

§ 102(e) Date: Aug. 7, 1991

[87] PCT Pub. No.: WO90/08163

PCT Pub. Date: Jul. 26, 1990

Related U.S. Application Data

[63] Continuation of application No. 07/720,771, Aug. 7, 1991, abandoned.

[30] Foreign Application Priority Data

Jan. 12, 1989 [DE] Germany ............................. P 3900770
Jan. 11, 1990 [WO] WIPO ...................... PCT/EP90/00063
Oct. 17, 1995 [DE] Germany ............................ 195 38 634

[51] Int. Cl.$^6$ ...................................................... C12D 21/04
[52] U.S. Cl. .................. 435/69.4; 435/69.7; 435/252.33; 514/12; 530/399; 530/402; 530/408; 530/412; 530/417
[58] Field of Search ..................................... 530/350, 399, 530/402, 408, 412, 417; 514/2, 8, 12; 536/23.5; 435/69.4, 69.7, 252.33, 320.1

[56] References Cited

FOREIGN PATENT DOCUMENTS 259632  3/1988  European Pat. Off. .
288307  10/1988  European Pat. Off. .

OTHER PUBLICATIONS

Hoppe, J. et al., *Biochemistry*, 28(7): 2956–2960, 1989.
Wang, J.Y. et al., *J. Biol. Chem.*, 259 (17): 10645–10648, 1984.
Devare, S. G. et al., *Cell*, 36(1): 43–50, 1984.

*Primary Examiner*—Patricia A. Duffy
*Attorney, Agent, or Firm*—Brooks & Kushman P.C.

[57] ABSTRACT

The invention relates to a process for the preparation of PDGF-A and to biologically active PDGF-AA and PDGF-AB.

12 Claims, 6 Drawing Sheets

Fig. 1

SIEEABPABCKTRTVIYEIPRSQVDPTSANFLIWPPCVEBKRCTGCCNT

SSVKCQPSRBHHRSVKVAKVEYVRKKPKLKEVQVRLEEHLECACATTSL

NPDYREEDTDVR

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
      (A) LENGTH:        110 residues
      (B) TYPE:          amino acid
      (C) STRANDEDNESS:  Not Relevant
      (D) TOPOLOGY:      linear    (ii) MOLECULE TYPE:       Protein    (iii) HYPOTHETICAL:       Yes    (iv) ANTI-SENSE:          No    (v) FRAGMENT TYPE:

(vi) ORIGINAL SOURCE:
      (A) ORGANISM:
      (B) STRAIN:             E. Coli
      (C) INDIVIDUAL ISOLATE:
      (D) DEVELOPMENTAL STAGE:
      (E) HAPLOTYPE:
      (F) TISSUE TYPE:
      (G) CELL TYPE:
      (H) CELL LINE:
      (I) ORGANELLE:

(vii) IMMEDIATE SOURCE:
      (B) CLONE:         PDGF-A    (xi) SEQUENCE DESCRIPTION: SEQ ID NO: 1:

Ser Ile Glu Glu Ala Val Pro Ala Val Cys
1               5                   10

Lys Thr Arg Thr Val Ile Tyr Glu Ile Pro

```
                    15                  20
Arg Ser Gln Val Asp Pro Thr Ser Ala Asn
                25                  30

Phe Leu Ile Trp Pro Pro Cys Val Glu Val
                35                  40

Lys Arg Cys Thr Gly Cys Cys Asn Thr Ser
                45                  50

Ser Val Lys Cys Gln Pro Ser Arg Val His
                55                  60

His Arg Ser Val Lys Val Ala Lys Val Glu
                65                  70

Tyr Val Arg Lys Lys Pro Lys Leu Lys Glu
                75                  80

Val Gln Val Arg Leu Glu Glu His Leu Glu
                85                  90

Cys Ala Cys Ala Thr Thr Ser Leu Asn Pro
                95                  100

Asp Tyr Arg Glu Glu Asp Thr Asp Val Arg
                105                 110

(2) INFORMATION FOR SEQ ID NO: 2:

(i) SEQUENCE CHARACTERISTICS:
        (A) LENGTH:        102 residues
        (B) TYPE:          amino acid
        (C) STRANDEDNESS:  Not Relevant
        (D) TOPOLOGY:      linear (ii) MOLECULE TYPE:    Protein (iii) HYPOTHETICAL:    Yes (iv) ANTI-SENSE:       No (v) FRAGMENT TYPE:

(vi) ORIGINAL SOURCE:
        (A) ORGANISM:
        (B) STRAIN:              E. Coli
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (B) CLONE:         PDGF-A (ix) FEATURE:
        (D) OTHER INFORMATION:

(xi) SEQUENCE DESCRIPTION: SEQ ID NO: 2:

Ile Ala Glu Cys Lys Thr Arg Thr Glu Val
1               5                   10

Phe Glu Ile Ser Arg Arg Leu Ile Asp Arg
                15                  20

Thr Asn Ala Asn Phe Leu Val Trp Pro Pro
                25                  30

Cys Val Glu Val Gln Arg Cys Ser Gly Cys
                35                  40

Cys Asn Asn Arg Asn Val Gln Cys Arg Pro
                45                  50
```

```
Thr Gln Val Gln Leu Arg Pro Val Gln Val
                55                  60

Arg Lys Ile Glu Ile Val Arg Lys Lys Pro
                65                  70

Ile Phe Lys Lys Ala Thr Val Thr Leu Glu
                75                  80

Asp His Leu Ala Cys Lys Cys Glu Thr Val
                85                  90

Ala Ala Ala Arg Pro Val Thr Arg Ser Pro
                95                  100

Leu Asn
    102
```

(2) INFORMATION FOR SEQ ID NO: 3:

(i) SEQUENCE CHARACTERISTICS:
        (A) LENGTH:          109 residues
        (B) TYPE:            amino acid
        (C) STRANDEDNESS:    Not Relevant
        (D) TOPOLOGY:        linear    (ii) MOLECULE TYPE:       Protein   (iii) HYPOTHETICAL:        Yes    (iv) ANTI-SENSE:          No     (v) FRAGMENT TYPE:

(vi) ORIGINAL SOURCE:
        (A) ORGANISM:
        (B) STRAIN:          E. Coli
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (B) CLONE:           PDGF-A    (ix) FEATURE:
        (D) OTHER INFORMATION:

(xi) SEQUENCE DESCRIPTION: SEQ ID NO: 3:

```
Ser Leu Gly Ser Leu Thr Ile Ala Glu Pro
  1             5                   10

Ala Met Ile Ala Glu Cys Lys Thr Arg Thr
                15                  20

Glu Val Phe Glu Ile Ser Arg Arg Leu Ile
                25                  30

Asp Arg Thr Asn Ala Asn Phe Leu Val Trp
                35                  40

Pro Pro Cys Val Glu Val Gln Arg Cys Ser
                45                  50

Gly Cys Cys Asn Asn Arg Asn Val Gln Cys
                55                  60

Arg Pro Thr Gln Val Gln Leu Arg Pro Val
                65                  70

Gln Val Arg Lys Ile Glu Ile Val Arg Lys
                75                  80

Lys Pro Ile Phe Lys Lys Ala Thr Val Thr
                85                  90
```

-continued

```
Leu Glu Asp His Leu Ala Cys Lys Cys Glu
                95                  100
Thr Val Ala Ala Ala Arg Pro Val Thr
                105             109
```

PDGF-AB, PREPARATION PROCESS AND PHARMACEUTICALS CONTAINING THEM

This application is a continuation of application Ser. No. 07/720,771, filed Aug. 7, 1991, now abandoned.

BACKGROUND OF THE INVENTION

1. Field of the Invention

The invention relates to a process for the preparation of PDGF-A and biologically active PDGF-AA and PDGF-AB.

2. Brief Description of Related Art

Platelet derived growth factor (PDGF) is a major mitogen in serum which promotes growth of fibroblasts and smooth muscle cells in vitro. In vivo, PDGF is stored in the a granules of the platelets and released after stimulation of the platelets. Highly purified PDGF is a basic protein which displays a considerable heterogeneity with regard to its molecular weight (27,000 to 31,000 d). The reasons for this heterogeneity are aging, processing and the existence of various isoforms of type AA, AB or BB. The biological activity of all these forms is destroyed by reduction of the disulfide bridges. Human PDGF from platelets consists principally of AB heterodimers (Heldin, C.-H. & Westermark, B. (1984) Cell, 37, 9–20; Deuel, T. F., Tong, B. D. & Huang, J. S. (1985) Current Topics in Cellular Regulation, 26, 51–61; and Ross, R., Raines, E. W. & Bowen-Pope, D. F. (1986) Cell, 46, 155–169.).

Amino-acid sequencing in conjunction with DNA sequencing of the genes have shown that A and B are homologous (Betsholtz et al. Nature 320, 695–699, 1986). PDGF-B is virtually identical to the transformed gene product $P_{28}^{v\text{-}sis}$ of simian sarcoma virus (SSV). Corresponding homodimers of type BB have been detected in SSV-transformed cells and showed properties similar to those of PDGF from platelets. However, these BB dimers were secreted to only a small extent from the infected cells. PDGF-AA forms are, by contrast, secreted efficiently by producing cells (Heldin et al. Nature, 319, 511–514, 1986). There is an increasing amount of evidence that the three isoforms, AA, AB and BB, assume different functions. Thus, for detailed investigations, it was necessary to develop a process for producing larger quantities of PDGF-A, PDGF-B, PDGF-AA and PDGF-AB.

Compare EP-A-0 288 307 for the use of PDGF for wound treatment.

SUMMARY OF THE INVENTION

According to one embodiment, the invention relates to PDGF-A (monomer) or biologically active (growth-stimulating) PDGF-AA (dimer), which can be prepared in such a way that I) *E. coli*, comprising a hybrid vector which is formed from pEX and foreign DNA which encodes the following fusion protein:

(a) a fusion protein composed of p-galactosidase and PDGF-A of the following amino-acid sequence (i) (SEQ ID NO:1)

SIEEAVPAVCKTRTVIYEIPRSQVDPT-
SANFLIWPPCVEVKRCTGCCNT

SSVKCQPSRVHHRSVKVAKVEYVRKKP-
KLKEVQVRLEEHLECACATTSL

NPDYREEDTDVR                                   (i)

or (b) a fusion protein according to (a), in which any desired amino acid is absent, in which any desired amino acid has been replaced by any other desired amino acid or in which any desired additional amino acid has been provided at any desired point, or (c) a fusion protein according to (a) or (b), in which the C terminus or the N terminus has been deleted or supplemented by up to 14 amino acids;

is used for the expression of a fusion protein as dimer of the monomers, according to (a), (b) and/or (c), II) the formed fusion protein (if appropriate after reduction) is chemically cleaved, and a monomer of the amino-acid sequence according to (I) (a) or a corresponding monomer in which any desired amino acid can be absent, any desired amino acid can be replaced by any other desired amino acid, any desired additional amino acid can be provided at any desired point, and/or the C terminus or the N terminus can be deleted or supplemented by up to 14 amino acids, is liberated, III) the thiol groups are protected by sulfonation, IV) the protected monomer is purified by chromatography, V) the sulfo groups in the purified and protected monomer are reduced and, where appropriate, furthermore VI) the deprotected monomer is dimerized by formation of disulphide bridges and then VII) the formed dimer is purified by chromatography.

According to another embodiment, the invention relates to biologically active (growth-stimulating) PDGF-AB, which can be prepared by employing in stage (III) as detailed above PDGF-A as detailed above in stage (II) and PDGF-B of the following amino-acid sequence (ii) (SEQ ID NO:2) or (iii) (SEQ ID NO:3)

```
              20        30        40        50        60   (ii)
   IAECKTRTEVFEISRRLIDRTNANFLVWPPCVEVQRCSGCCNNRNVQC 70        80        90       100       110
   RPTQVQLRPVQVRKIEIVRKKPIFKKATVTLEDHLACKCETVAAARPVTRSPLN 1        10        20        30        40        50        60   (iii)
   SLGSLTIAEPAMIAECKTRTEVFEISRRLIDRTNANFLVWPPCVEVQRCSGCCNNRNVQC 70        80        90       100       110
   RPTQVQLRPVQVRKIEIVRKKPIFKKATVTLEDHLACKCETVAAARPVT
``` or of an amino-acid sequence according to (i) or (ii) in which any desired amino acid is absent, in which any desired amino acid is replaced by any other desired amino acid, in which any desired additional amino acid is provided at any desired point and/or in which the C terminus or the N terminus is deleted or supplemented by up to 14 amino acids, and the process as detailed above in stages (III) to (VII) is carried out, and PDGF-AB is obtained.

According to another embodiment, the invention relates to a process for the preparation of PDGF-A (monomer) and optionally biologically active (growth-stimulating) PDGF-AA (dimer), which is characterized in that I) E. coli, comprising a hybrid vector which is formed from pEX and foreign DNA which encodes the following fusion protein:

(a) a fusion protein composed of β-galactosidase and PDGF-A of the following amino-acid sequence (SEQ ID NO:1)

SIEEAVPAVCKTRTVTYEIPRSQVDPT-
SANFLIWPPCVEVKRCTGCCNT

SSVKCQPSRVHHRSVKVAKVEYVRKKP-
KLKEVQVRLEEHLECACATTSL

NPDYREEDTDVR or (b) a fusion protein according to (a), in which any desired amino acid is absent, in which any desired amino acid has been replaced by any other desired amino acid or in which any desired additional amino acid has been provided at any desired point, or (c) a fusion protein according to (a) or (b), in which the C terminus or the N terminus has been deleted or supplemented by up to 14 amino acids;

is used for the expression of a fusion protein as dimer of the monomers, according to (a), (b) and/or (c), II) the formed fusion protein (if appropriate after reduction) is chemically cleaved, and a monomer of the amino-acid sequence according to (I) (a) or a corresponding monomer in which any desired amino acid can be absent, any desired amino acid can be replaced by any other desired amino acid, any desired additional amino acid can be provided at any desired point, and/or the C terminus or the N terminus can be deleted or supplemented by up to 14 amino acids, is liberated, III) the thiol groups are protected by sulfonation, IV) the protected monomer is purified by chromatography, V) the sulfo groups in the purified and protected monomer are reduced and, where appropriate, furthermore VI) the deprotected monomer is dimerized by formation of disulfide bridges and then VII) the formed dimer is purified by chromatography.

According to another embodiment of the invention, it is possible to employ in stage (III) two monomers (PDGF-A) which are different.

According to another embodiment of the invention, it is possible to employ in stage (III) PDGF-A which was produced in stage (II) and PDGF-B as described above.

Figure 3:
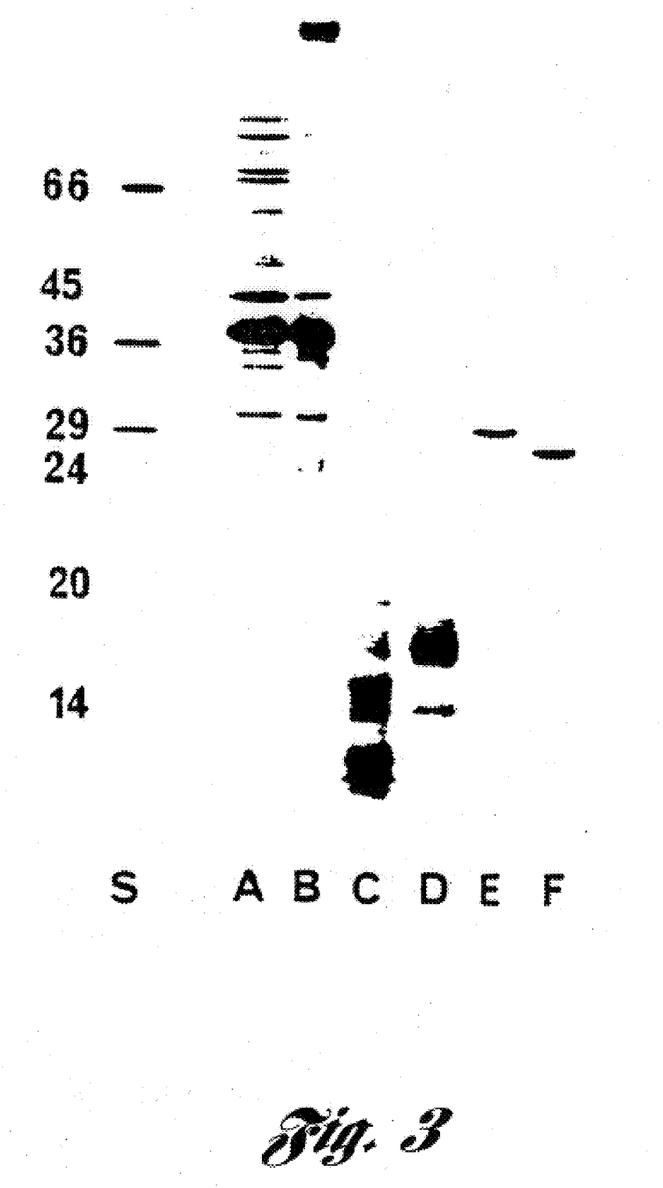
FIG. 3: Analysis by SDS gel electrophoresis of the expression of PDGF-A in E. coli and of the purification steps.

As FIG. 3 shows, the modified pEX-2 vector promotes high-level expression of the cro-β-gal-PDGF-A fusion protein. Deletion of about 80% of the lacz gene results in formation of a small fusion protein of 40,000 d which has a PDGF-A content of more than 50%. Despite these favorable preconditions, the yields of rPDGF-AA are comparatively low, at 0.2 mg/l of culture. Three reasons are responsible for this.

1) The cells must be induced at a low density and therefore reach an ultimate density of only 1.5 $OD_{550}$. Other induction or growth conditions had a significantly adverse effect on the expression of the fusion protein.

2) The CNBr cleavage at the MSIEE . . . site does not take place completely.

3) A loss of yield occurs owing to the dimerization.

Figure 5:
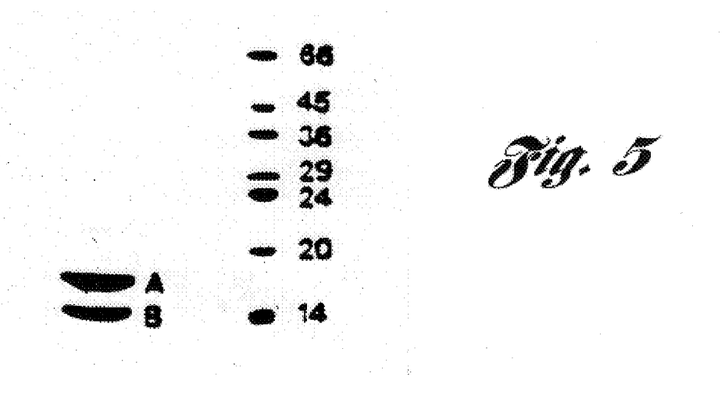
FIG. 5: SDS gel electrophoresis of purified rPDGF-AB after reduction with 2-mercaptoethanol. The bands which correspond to rPDGF-A and rPDGF-B are indicated.

The biological activity of rPDGF-AB is comparable with that of human platelet PDGF and rPDGF-BB from E. coli. The activity of rPDGF-AA is about 10 times less (cf. FIG. 5).

According to another embodiment, the invention relates to a pharmaceutical for wound treatment, which is characterized by PDGF-A, PDGF-AA and/or PDGF-AB according to the preceding description as active substance, where appropriate in combination with customary excipients, diluents and/or one or more other growth factors or substances promoting wound healing. Insuline (sic) like growth factor (IGF) is an example of another growth factor.

BRIEF DESCRIPTION OF THE DRAWINGS

The invention is explained in more detail hereinafter with examples and figures. Further details of the preparation can be found (lacuna) Hoppe et al. in Biochem., 28 (1989) 2956–2960 and Eur. J. Biochem., 778 (1989). Moreover the sequences (i) to (iii) can also be prepared by synthesis, for example using oligopeptide synthesis machines.

White boxes: cro-lacZ gene

Grey boxes: gene region for the mature PDGF-A

Black boxes: gene regions for pre-prosequences

Wavy line: m13mp19 sequences $P_R$: bacteriophage lambda promoter; cro-lacZ: cro-β-galactosidase fusion protein; $t_{fd}$: phage transcription terminator.

A) Lysate of E. coli cells

B) Inclusion bodies

C) CNBr fragments

D) Monomeric rPDGF-A after HPLC purification

E) Dimeric rPDGF-AA after final purification

F) Dimeric rPDGF-AB after final purification

Monomeric rPDGF-A and -B were mixed in the stated ratios and subjected to the renaturation conditions. After one day, 8 μg were analyzed by SDS gel electrophoresis.

FIG. 6: Biological activities of recombinant PDGF isoforms. (6A) Stimulation of [$^3$H]-thymidine incorporation in AKR-2B mouse fibroblasts by rPDGF-AA (black boxes), rPDGF-AB (black circles) and rPDGF-BB (black triangles). A background of 2800 cpm was subtracted. (6B) Binding of $^{125}$I-rPDGF-AA (black boxes), $^{125}$I-rPDGF-AB (black dots) and $^{125}$I-rPDGF-BB (black triangles) to AKR-2B mouse fibroblasts. rPDGF-BB was labeled with Bolton-Hunter reagent. B/F=bound/free factor.

DETAILED DESCRIPTION OF THE INVENTION

Abbreviations

HBS: saline buffered with Hepes
PBS: saline buffered with phosphate
PDGF: platelet-derived growth factor (=growth factor from platelets)
rPDGF-AA, -AB, -BB: recombinant PDGF of isoforms AA, AB and BB
P28$^{v\text{-}sis}$: transforming protein of simian sarcoma virus
cro-β-gal: fusion protein composed of cro repressor and β-galactosidase
FCS: fetal calf serum
RF: replication form

Materials pMVW: cf. FEBS Letters, 198 (1986) 344, 345
pEX1 (plasmid): Genofit Heidelberg; cf. also EMBO J., 3 (1984) 1429–1434
pEX2 (plasmid): Genofit, Heidelberg
E. coli NF1: cf. EMBO J., 3 (1984) 1429–1434
E. coli JC 236: BioRad
E. coli JM 103: Pharmacia
m13mp18: Pharmacia
m13mp19: Pharmacia
mutagenesis kit including E. coli CJ 236: BioRad
pPGF-2: FEBS Letters, 229 (1987) 243, 244

Guanidine hydrochloride and tris were from Sigma, formic acid, 2-propanol, acetonitrile, trifluoroacetic acid from Merck. Sephacryl S-200 was from Pharmacia, the Si-300 polyolbutyl chromatography column and ampicillin from Serva, medium and supplements from Gibco and radiochemicals from Amersham.

Biological systems

Growth-stimulating activity was determined by the method of Shipley et al. Cancer Res., 49, 710–716, (1984).

Analytical methods

Gel electrophoreses were carried out as described (13.5 percent gels) (Hoppe et al. Eur. J. Biochem., 155, 259–264, 1986). Amino-acid analyses were determined using an analyzer (LC2000 from Biotronic). Amino-terminal sequence analyses were determined using a gas-phase analyzer (470A from Applied Biosystems). The protein content was determined by the methods of Bradford Anal. Biochem. 72, 248–253, (1976) or Redinbaugh Analyt. Biochem. 153, 267–271, (1986).

EXAMPLE 1

PDGF-A and PDGF-AA

Construction of an expression vector for PDGF-A sequences

Figure 1:
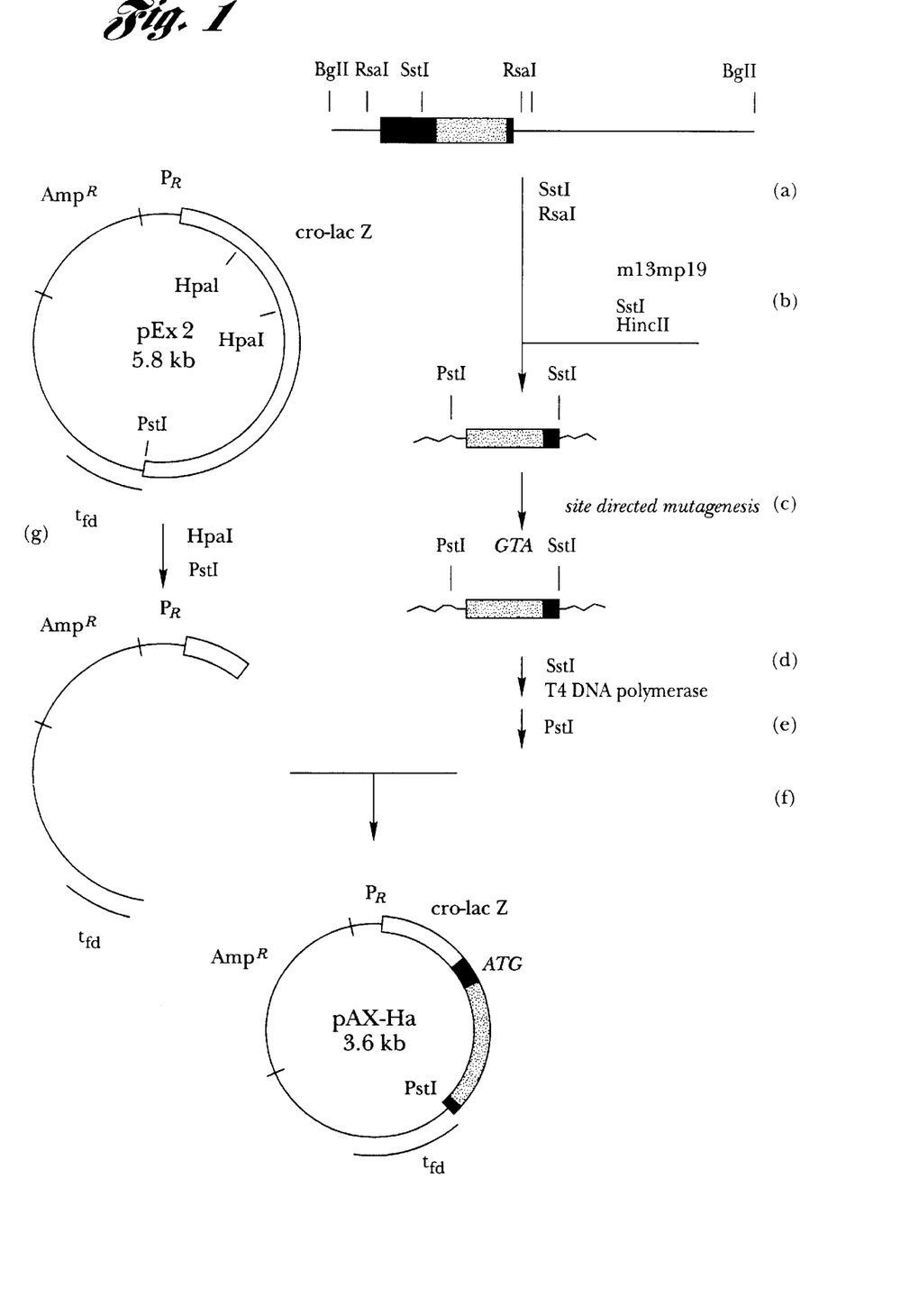
FIG. 1: Strategy for the construction of the plasmid pAx-HA.
Figure 2:
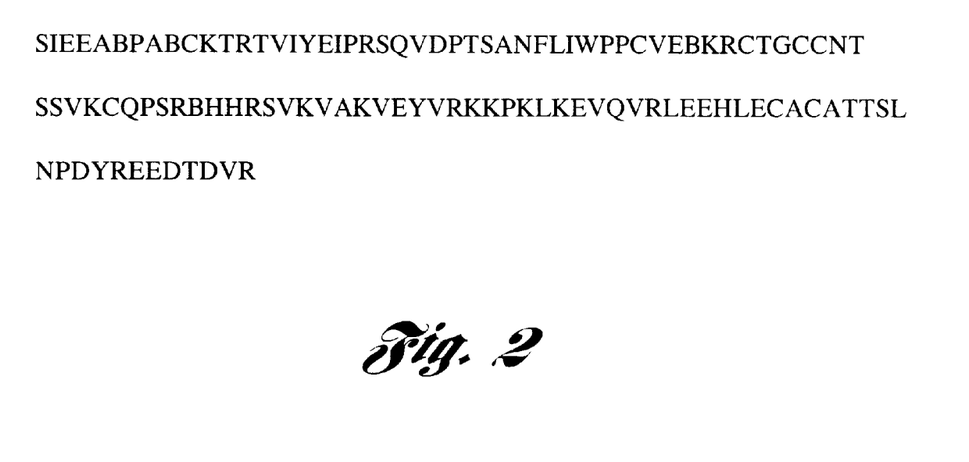
FIG. 2: Amino-acid sequence of the expressed PDGF-A. (SEQ ID NO:1) A=alanine, D=aspartic acid, E=glutamic acid, F=phenylalanine, G=glycine, H=histidine, I=isoleucine, K=lysine, L=leucine, M=methionine, N=asparagine, P=proline, Q=glutamine, R=arginine, S=serine, T=threonine, V=valine, W=tryptophan, Y=tyrosine.

A 2 kb-long BglI fragment from clone pPGF-2 (Hoppe et al. FEBS Lett., 223, 243–246, 1987) which contains the region coding for PDGF-A was cleaved with SstI and RsaI (FIG. 1 line a). The 460 b-long fragment obtained in this way was integrated into the phage m13mp19 which had previously been cleaved with SstI and HincII (FIG. 2 line b). After transformation into the host strain JM103, the resulting colonies were tested for correct integration into the phage DNA. The strain CJ236 (20 ml) was then infected with 3×10$^6$ of the phages obtained in this way. Subsequently uracil-containing phages were isolated as described (BioRad manual for directed mutagenesis). Single-stranded phage DNA was then hybridized with the primer CGG AGG AAG ATG AGC ATC GAG GAA G in order to mutate the arginine in position 76 (AGA) into a methionine (ATG) (FIG. 1 line c). After synthesis of the second strand using T4 DNA polymerase and transformation into the host strain JM 103, the region coding for PDGF-A was analyzed in four phages by DNA sequencing.

Two phages contained the required exchange. One of these phages was used to prepare RF DNA. This plasmid DNA was digested with SstI. Protruding ends were removed by T4 DNA polymerase treatment (FIG. 1 line d), and a 460 b-long fragment was liberated by PstI cleavage (FIG. 1 line e). This fragment was integrated into the HpaI/PstI sites of the expression vector pEX-2 (FIG. 1 line f). This HpaI/PstI digestion of the pEX-2 plasmid (FIG. 1 line g) resulted in deletion of about 2600 b of the lacz gene and reduced the size of the cro-β-gal protein to 18,000 d. The strains obtained after transfection in the host strain NF1 were cultivated in LB medium at 30° C. until the optical density was 0.2 OD (550 nm). Production of the cro-β-gal-PDGF-A fusion protein was induced by increasing the temperature to 42° C. After 2 hours, the cells were harvested and proteins were analyzed by SDS gel electrophoresis. A strain with high-level expression of the PDGF-A sequences was isolated. The plasmid was called pAX-HA.

Culturing of cells and preparation of inclusion bodies

E. coli cells were cultured in LB medium with 50 to 100 μg of ampicillin/ml in 1 l cultures at 30° C. until the optical density was 0.2 OD (440 nm) and then shaken at 42° C. for a further 3 hours. The cells were harvested by centrifugation (10 min at 5000×g) and suspended in 20 ml of tris-HCl (20 mM) and EDTA (0.5 mM) of pH 7.8. A culture of 20 to 30 l was cultured for a typical preparation. The cells were disrupted by passing twice through a press (Ribi from Sorvall) under 20,000 psi or by ultrasound treatment. Inclusion bodies were obtained after addition of 2% Triton X100 (final concentration) by centrifugation (10 min at 6000×g).

Reduction and CNBr cleavage

Inclusion bodies from 20 to 30 l of culture were dissolved in 100 ml of 50 mM tris-HCl (50 mM) of pH 7.8 with 2% SDS and 2% 2-mercaptoethanol (about 1 h at 37° C.). Small amounts of insoluble material were removed by centrifugation at 20,000×g for 30 min. 2 volumes of acetone were added to the supernatant at 0° C. After 15 min at 0° C., a voluminous precipitate was removed by centrifugation (10 min at 6000×g) and was dissolved in 80 ml of formic acid (100%). Then 20 ml of H$_2$O were added. Insoluble material was removed at 50,000×g for 1 h. 1 g of CNBr and 200 μl of 2-mercaptoethanol were added to the supernatant. The reaction was carried out at room temperature overnight. The solution was dried in a rotary evaporator. The residue was taken up in 80 ml of guanidine hydrochloride (6 M), and the pH was adjusted to 7.5 by addition of 30% NaOH. As an alternative, the cleavage can also be carried out in the presence of 6 M guanidine hydrochloride. Cleavage is followed by dialysis against 10 l of H$_2$O. The dialysate is adjusted with guanidine hydrochloride to the final concentration of 6 M.

S-Sulfonation 1 g of Na$_2$SO$_3$ and 0.25 g of Na$_2$S$_2$O$_6$ were added to the resulting solution. The mixture was left at room temperature for 5 h. The insoluble material was removed by centrifugation (1 h at 50,000×g).

Purification of S-sulfonated monomeric rPDGF-A

The solution obtained above was loaded onto a column packed with Sephacryl S200 (dimension 5 cm diameter×100 cm). Used as eluent was guanidine hydrochloride (4 M) and tris-HCl (50 mM) of pH 7.4. The flow rate was 160 ml/h. Fractions of 15 ml were collected. Aliquots of these fractions were analyzed by SDS gel electrophoresis. Those fractions which exhibited proteins with a molecular weight of about 17 kd were combined and dialyzed against 5 l of H$_2$O overnight. During the dialysis there was formation of a precipitate which could be substantially dissolved by addition of formic acid to a final concentration of 10%. Insoluble material was removed by centrifugation (20 min at 200,000× g). The supernatant (about 150 ml) was loaded onto an HPLC column (2 cm diameter×25 cm; reverse phase: Si-300-polyolbutyl 5 μm) (from Serva) at a flow rate of 2.5 ml/min. Sample loading was followed by washing with about 2 column volumes. rPDGF-A monomer was eluted by a linear gradient of 10% formic acid/H$_2$O against 10% formic acid/60% 2-propanol/30% H$_2$O at a flow rate of 2.5 ml/min for 180 min. rPDGF-A eluted early after 40 to 50 min. Appropriate fractions were combined and dialyzed against 5 l of H$_2$O.

Dimerization to rPDGF-AA and purification

S-sulfonated monomeric rPDGF-A was adjusted to a concentration of 0.4 mg/ml. Subsequently, urea was added to a final concentration of 2 M and then glutathione (5 mM) and oxidized glutathione (0.5 mM). The pH was adjusted to 7.8 by addition of tris-HCl (if necessary tris base) (final concentration about 50 mM). The reaction mixture was left at room temperature for 2 days.

Dimeric rPDGF-AA was purified by ion exchange chromatography. For this, the dimerization mixture was dialyzed against 1 l of Na acetate (20 mM; pH 5.1) and loaded onto a column packed with Fractogel TSK SP 650. The column was equilibrated in Na acetate (20 mM; pH 5.1), choosing a ratio of 5 mg of protein/ml of column material. After a washing step at pH 5.1 with Na acetate (20 mM) and NaCl (100 mM), elution was carried out at pH 5.1 with a linear gradient of NaCl (100 mM to 400 mM) in Na acetate (20 mM). The gradient volume was ten times the column volume.

Dimeric forms eluted later than monomeric species.

Biologically active (growth stimulating) PDGF-BB is characterized by the following amino acid sequence of its monomers:

```
1        10        20        30        40        50        60
SLGSLTIAEPAMIAECKTRTEVFEISRRLIDRTNANFLVWPPCVEVQRCSGCCNNRNVQC 70        80        90        100       110
RPTQVQLRPVQVRKIEIVRKKPIFKKATVTLEDHLACKCETVAAARPVTRSPLN
``` where the monomers can, independently of each other, lack any amino acid, and any amino acid can be replaced by any other amino acid, and/or any additional amino acid can be provided at any place. In particular, the C termini of both monomers can be modified, independently of each other, by the deletion or addition of up to 14 amino acids.

A method is provided for the preparation of PDGF-B with the above amino acid sequence (monomer) and optionally for the preparation of biologically active (growth stimulating) PDGF-BB (as a dimer), in which 1) using *E. coli* which comprises a hybrid vector which is constructed from pEX and foreign DNA, the following fusion protein is coded:

a) a fusion protein made of β-galactosidase and PDGF-B with the amino acid sequence immediately prior, or b) a fusion protein according to (a), which can lack any amino acid, in which any amino acid can be replaced by any other amino acid, or in which any additional amino acid can be added at any place, and/or c) a fusion protein, in which the C termini have been modified, independently of each other, by the deletion or addition of up to 14 amino acids, a fusion protein according to (a), (b), or (c) is expressed, II) the fusion protein formed is chemically cleaved (optionally after reduction), releasing a monomer III) the thiol groups are protected by sulfonation, IV) the protected monomer is purified by gel permeation chromatography and/or reverse phase chromatography, V) the sulfo groups of the purified and protected monomer are reduced, and, furthermore, VI) the unprotected monomer is dimerized by the formation of disulfide bridges, and then VII) the formed dimer is purified by reverse phase chromatography and/or ion exchange chromatography.

For step (I), *E. coli* can be used with a hybrid vector, constructed using pEX, for example pEX 1, pEX 2, or pEX 3; compare to Stanley & Lucio 1984. As a result of the pEX plasmids, the expression of cro-β-gal×protein is considerably increased. It accounts for approximately 30% of the total cell protein. To increase the yield of PDGF-B, it is preferred to remove large sections of the expression region, without thereby negatively affecting the level of expression. PDGF-B-expressing clones can easily be identified by an increase in the molecular weight of approximately 1 5 kd in the fusion protein.

In step (II), the cleavage is preferably carried out using bromocyanide. Any inclusion bodies which may form are dissolved before the cleavage, for example by reduction (during which any existing S-S bridges are cleaved).

In step (III), the sulfonation can be carried out in the presence of sulfite and dithimonate.

In step (IV), the gel permeation chromatography can be carried out in the presence of a denaturing agent, for example guanidine hydrochloride, for example at a molarity of 1–6M.

It is preferred that Steps (V) and (VI) are performed simultaneously, for example in the presence of a) urea (for example at a molarity of up to 4M) and b) a thiol reagent, such as 2-mercaptoethanol (for example at a concentration of up to 2%), glutathione (for example at a molarity of up to 100 mM) and dithiothreitol and dithioerythiol (for example at a molarity of up to 100 mM).

The invention is further explained below with reference to an example and FIG. 7.

Figure 7:
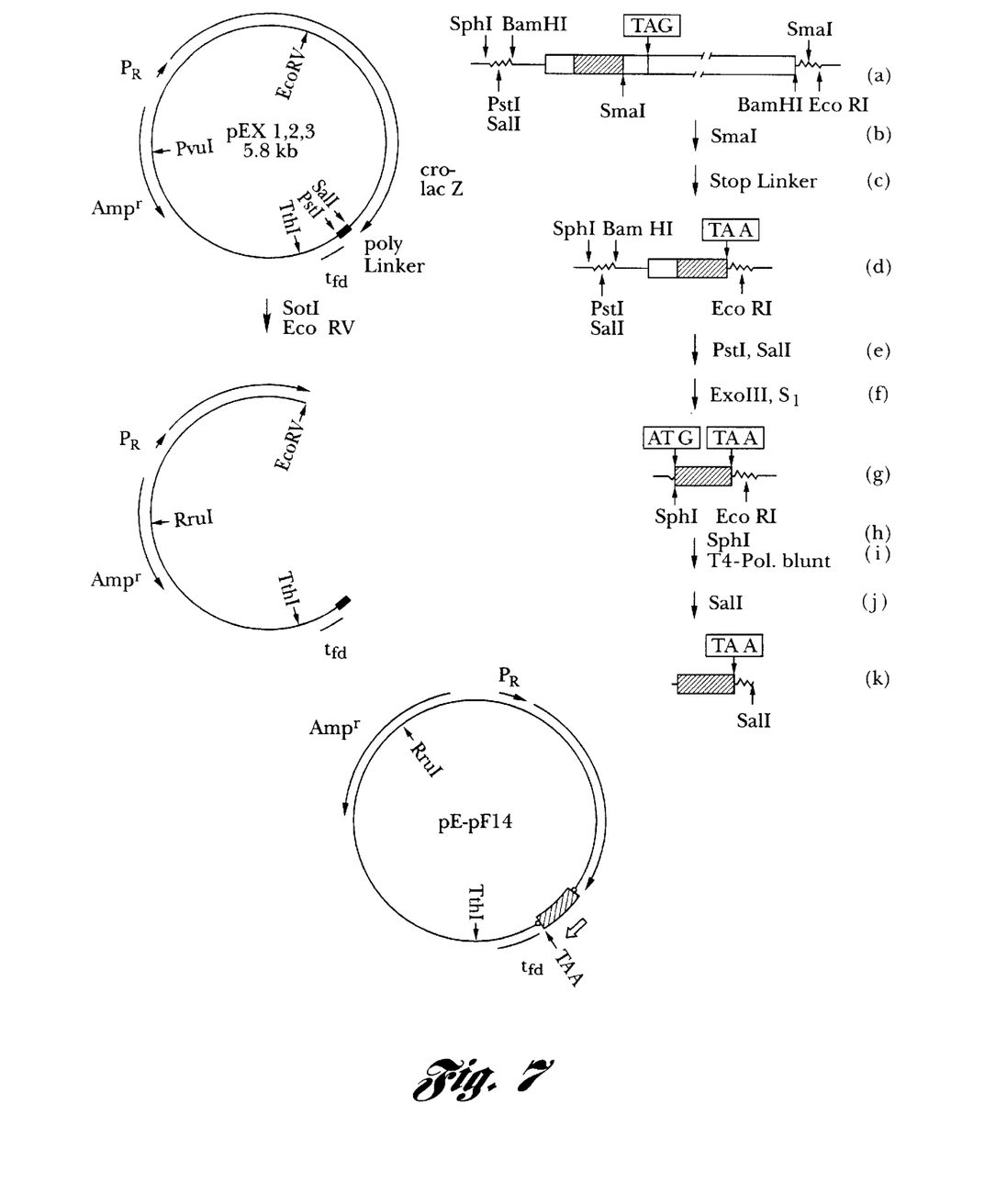
FIG. 7: Strategy for the construction of the plasmid pE-PF 14.

FIG. 7: Strategy for the construction of the plasmid pE-PF 14.

The 2-kb long BamHI fragment obtained from the plasmid pMWV-2 was integrated in reverse direction into the phage M13 mp 18 (open box: c-cis-mRNA sequences); crosshatched boxes: regions for mature PDGF-B). The long 3' region, which includes the original stop codon TAG, was removed with SmaI digestion enzyme. A stop linker was introduced into this region. 5' regions were removed with the digestion enzyme exonuclease III. After one passage thorough the vector pJLA504, PDGF coding sequences coding for PDGF-B in the reading frame were integrated at the SalI/EcoRV sites of the vector pEX 1. $P_R$=bacteriophage promoter; cro'-lacZ=cro-β-galactosidase fusion protein; tdf= phage transcription terminator.

Amino acid sequences of PDGF-B and rPDGF-B are:

```
1       10        20        30        40        50        60
SLGSLTIAEPAMIAECKTRTEVFEISRRLIDRTNANFLVWPPCVEVQRCSGCCNNRNVQC (SEQ ID NO:3)

IAECKTRTEVFEISRRLIDRTNANFLVWPPCVEVQRCSGCCNNRNVQC (SEQ ID NO:2)

70        80        90       100       110
RPTQVQLRPVQVRKIEIVRKKPIFKKATVTLEDHLACKCETVAAARPVT

RPTQVQLRPVQVRKIEIVRKKPIFKKATVTLEDHLACKCETVAAARPVTRSPLN
```

It should be noted that the first 12 amino acids have been removed by cleavage with CNBr in rPDGF-B. Furthermore, rPDGF-B contains 5 additional amino acids at the C terminus. Three of these amino acids differ from PDGF sequences, and originate from the stop linker at the SmaI cleavage site (see FIG. 7).

A=alanine, D=aspartic acid, E=glutamic acid, F=phenylalanine, G=glycine, H=histidine, I=isoleucine, K=lysine, L=leucine, M=methionine, N=asparagine, P=proline, O=glutamine, R=arginine, S serine, T=threonine, V=valine, W=tryptophan, Y=tyrosine.

Materials

E. coli JM103: Pharmacia

E coliNF1: see EMBO J., 3(1984) 1429–1434 pEX 1 (plasmid): Genofit Heidelberg; see also EMBO J., 3 (1984) 1429–1434

M13mp 18 (vector): Pharmacia; see also FEBS Letters, 198 (1986) 344–348, 345 pJLA504 (plasmid): see Gene, 52 (1907) 279–283, 280 pMVW-2 (plasmid): see FEBS Letters, 198 (1986) 344–348, 346

Guanidine hydrochloride and tris were from Sigma, formic acid, 2-propanol, acetonitrile, trifluoroacetic acid from Merck, Sephacryl S-200 from Pharmacia, chromatography column Si-300 polyolbutyl and ampicillin from Serva, medium and supplement from Gibco, and radiochemicals from Amersham.

Biological Systems

The growth stimulating activity was determined according to Shipley et al. (1984).

Analytical Methods

The gel electrophoresis was carried out as described (Hoppe et al. 1986) (13.5% gels). The amino acid analyses were performed with the analyzer LC2000 form Biotronic. The amino terminus sequence analyses were carried out with solid phase sequencer L12 (Sequemat). In this process, the protein was bound with its amino group to glass that had been activated with diisothiocyanate (Hoppe et al., 1986). Alternately, the sequences were determined with the gas phase analyzer 470A (Applied Biosystems). The protein content was determined according to the methods of Bradford (1976) or Redinbaugh & Turley (1986).

Construction of an Expression Vector

As the host, the strain NF1 was used (K12 delta-H1 delta trp lacZ⁻am), which contains integrated in it the defective lambda prophage (Nam 7 Nam 53 cl 857 delta-H1) (Stanley & Luzio). The starting material used was the BamHI DNA fragment (2 kb) from the clone pMVW-2 (Weich et al. 1986), which carries the DNA sequence coding for PDGF-B. This fragment was subcloned in the reverse direction at the BamHI site of the vector M13mp18. By digestion with SmaI (FIG. 7, line b), 3' sequences which are not translated and regions coding for the C terminus prosequences were removed. Then a translation stop linker (PL Biochemical) was integrated into the SmaI junction (FIG. 7, line f). 5' regions which code for the $NH_2$ terminus sequences were eliminated using the method of Henikoff (1984). In addition, the plasmid was digested with PstI and SalI (FIG. 7, line e) and subjected to a treatment with Exonuclease III (FIG. 7, line f). The remaining second strand was removed with S1 nuclease (FIG. 7, line f). Using the DNA polymerase/ Klenow fragment treatment, smooth ends were obtained, and then the plasmid was recycled by treatment with ligase. After transformation in the strain JM103, colonies were obtained. The extent of the cleavage by Exonuclease III was determined by the miniplasmid preparation and by sequencing of the plasmid DNA of this colony. The resulting plasmid contained an ATP start codon from the SphI cleavage site of the "multicloning site" of the M13mp18 vector in the reading frame with the PDGF-B sequence. The result was a slight modification of the $NH_2$ terminus (met-pro-leu-gly instead of ser-leu-gly). The sequences coding for PDGF-B were excised by partial digestion with SphI/EcoRI, and integrated into the plasmid pJLA504 (Schauder et al. 1987) (SphI/EcoRI) to obtain a SalI 3' end. This plasmid was then again partially digested with SphI (FIG. 7, line h). Projecting 3' ends were removed by a treatment with T4 polymerase (FIG. 7, line j). A 390-bp fragment, which contained the PDGF-B sequences, was isolated after the SalI digestion (FIG. 7, line j), and integrated into the SalI/EcoRV locations of the pEX 1 vector (FIG. 7, middle bottom section).

As a result of the Sail/EcoRV digestion of the plasmid pEX 1, 1097 nucleotides were removed, which coded for approximately ⅔ of the β-galactosidase. The deletion did not change the high expression level for cro-β-gal fusion protein.

For the identification of such clones, which are capable of expressing the cro-β-fusion protein with high yield, colonies obtained after the transformation into the strain NF1 were cultured in LB medium at 30° C. until the optical density was 0.3 (440 nm); the cultivation was then continued for 3 h at 42° C., to induce the production of cro-β-gal fusion proteins. Cells were lysed by ultrasound treatment, and dissolved in sodium dodecyl sulfate (SDS) and 2-mercaptoethanol. After polyacrylamide electrophoresis in the presence of sodium dodcyl sulfate, an intense band was obtained with numerous preparations, with a molecular weight of 65,000 d, which is indicative of the expression of PDGF sequences. The isolated plasmid was called pE-pF14.

Cultivation of cells and preparation of inclusion bodies

E. coli cells were cultured in LB medium with 50–100 $\mu$m/mL ampicillin in 1-L cultures at 30° C. until the optical density was 0.2 (440 nm), and then shaken at 42° C. for an additional 3 h. The cells were harvested by centrifugation (5000 g, 10 min), and suspended in EDTA (0.5mM) at pH 7.8. For a typical preparation, 20–30 L of culture were cultured. The cells were ruptured by two passes through a Ribi press (Sorvall) at 20,000 psi. The fusion protein consisting of parts of the cro repressor and of β-galactosidase, and PDGF-B (recombinant, monomeric growth factor from type B thrombocytes), forms inclusion bodies which were obtained by centrifugation (6000 g, 10 min) after the addition of 2% Triton X 100 (final concentration).

Reduction and CNBr cleavage

Inclusion bodies from 20–30 L of culture were dissolved in 100 mL Tris-HCl (50 mM; pH 7.8) with 2% SDS (sodium dodecyl sulfate) and 2% 2-mercaptoethanol (approximately 1 h, 37° C.). Small quantities of insoluble material were removed by centrifugation at 20,000 G for 30 min. 2 volumes of acetone at 0° C. were added to the supernatant. After 15 min at 0° C., a voluminous precipitate was removed by centrifugation (6000 G, 10 min), which was dissolved in 80 mL formic acid (100%). Then 20 mL of $H_2O$ were added, and insoluble material was removed by centrifugation at 50,000 G for 1 h. 1 g of CNBr and 200 µL of 2-mercaptoethanol were added to the supernatant. The reaction was carried out overnight at room temperature. The solution was evaporated to dryness on the rotary evaporator. The residue was dissolved in 80 mL of 6M guanidine hydrochloride, and the pH was adjusted to 7.5 by the addition of 30% NaOH.

Reference should be made to the fact that PDGF-B has only one methionine residue in position 12 in the $NH_2$ terminus part of the mature sequence. The cleavage of the cro-β-PDGF-B fusion protein at the methionine residue therefore produced fragments which were shortened by 12 amino acids. Furthermore, the introduction of the stop signal resulted in modifications of the protein at the C terminus.

S Sulfonation 1 g of $NA_2SO_3$ and 0.25 g of $Na_2S_2O_6$ were added to the obtained solution. The mixture was left standing for 5 h at room temperature. Insoluble material was removed by centrifugation (50,000 G, 1 h).

Purification of S-sulfonated monomeric rPDGF-B

The solution obtained above was applied for gel filtration to a column (size 5 cm diameter×100 cm), which was filled with Sephacryl S200. 4M guanidine hydrochloride with 50 mM tris-HCl, pH 7.4, was used as eluant. The flow rate was 160 mL/h. 15-mL fractions were collected. Aliquots of the fractions were analyzed by SDS gel electrophoresis, and fractions which contained proteins with a molecular weight of approximately 14 kd were purified and dialyzed overnight against 5 L of $H_2O$. During the dialysis, a precipitate formed, which could be largely dissolved by the addition of formic acid with a final concentration of 10%. Insoluble material was removed by centrifugation (20,000 G, 20 min). The supernatant (approximately 150 mL) was applied to an HPLC column (size 2 cm diameter×25 cm; reverse phase: Si-300-polyolbutyl, 5 µm, Serva) at a flow rate of 2.5 mL/min. After the application of the sample, a washing was performed with approximately 2 column volumes. rPDGF-B monomer was eluted using a linear gradient of 10% formic acid/$H_2O$ versus 10% formic acid, 60% 2-propanol and 30% $H_2O$ for 180 min at a flow rate of 2.5 mL/min. rPDGF-B eluted early, after 40–60 min. Corresponding fractions were purified, and dialyzed against 5 L of $H_2O$.

After the mentioned purifications by gel filtration and HPLC in reverse phase, approximately 2 mg of rPDGF monomer/L of culture were obtained; the latter product was found to be homogeneous by SDS gel electrophoresis, amino acid analysis, and $NH_2$ terminus sequence analysis.

EXAMPLE 2

PDGF-AB rPDGF-B was obtained according to P 38 34 079.8 or by the following modification. The BamH1 DNA fragment (2 kb) from the clone pMVW-2 (Weich et al. FEBS Lett., 198, 344–348, 1986), which contained c-sis, was subcloned with the reverse orientation in the vector M13mp18. The 3'-coding region of the PDGF-B chain was eliminated with SmaI. To eliminate the 5'-coding region of the c-sis gene, the plasmid was digested with PstI and SalI in order to form sticky 5' and 3' ends for digestion with exonuclease II in a known manner (Henikoff, Gene 28, 351–359, 1984). The second strand was eliminated by S1 digestion; the DNA to be inserted was provided with blunt ends by filling in with DNA polymerase I Klenow fragment. After ligation and transformation, colonies which embraced sequences homologous with PDGF-B were selected and sequenced in order to determine the extent of digestion by exonuclease III. A plasmid which contained the ATG start codon of the SpHI site of the M13mp18 multiple cloning site in reading frame with the PDGF-B sequence was isolated. Arg110 in the sequence of mature PDGF was mutated by means of directed mutagenesis (site directed mutagenesis) into a stop codon in accordance with the BioRad protocol.

The strain CJ236 (20 ml) was infected with 3×10$^6$ phages of M13mp18, and U-containing phages were isolated in a known manner. The single-stranded phage DNA was hybridized with the primer CGG CCT GTG ACC TGA AGC CCG G in order to mutate Arg110 into a stop codon. The second strand was synthesized after addition of 14 polymerase. Sequencing resulted in several strains which contained a stop codon in position 110. RF DNA was prepared from one of these strains and partially digested with SpHI. Protruding 3' ends of the SpHI site were converted into blunt ends by T4 polymerase treatment. A fragment with 350 base-pairs and containing the PDGF-B sequence was obtained by EcoRI digestion; this fragment was ligated into the EcoRI/ EcoRV site of pEX-2. Monomeric rPDGF-B was prepared in analogy to the preparation of rPDGF-A.

To prepare rPDGF-AB, the monomeric forms rPDGF-A and rPDGF-B were mixed in equimolar amounts (final concentration 0.4 mg/ml of protein). Compare Example 1 for the dimerization conditions and the purification.

Figure 4:
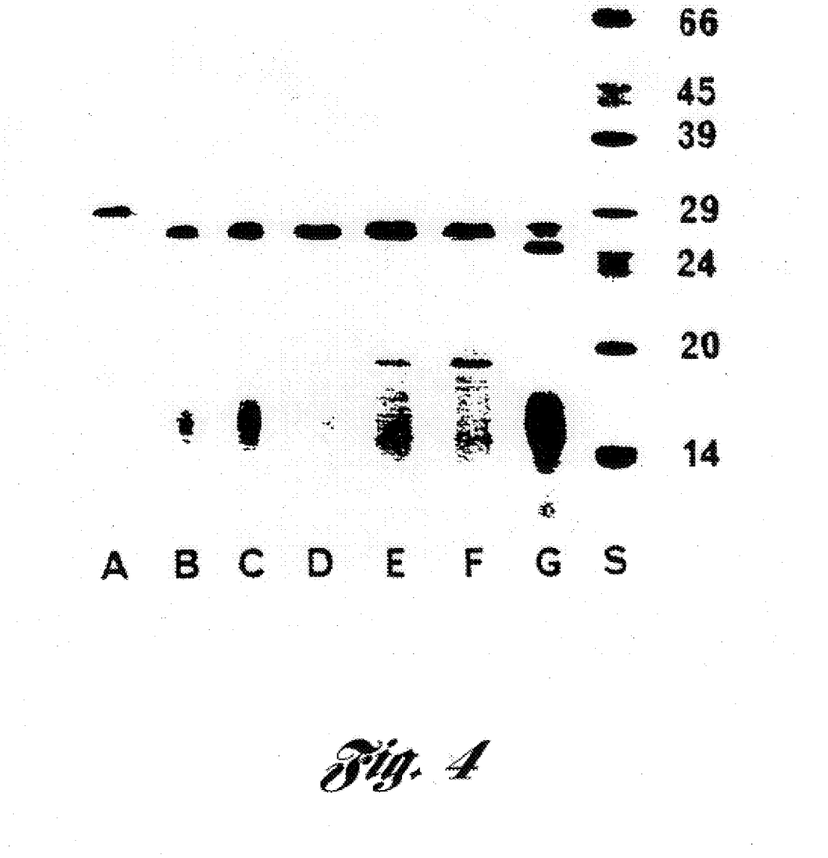
FIG. 4: Preferred formation of heterodimers from monomeric rPDGF-A or -B.

The renaturation yield is distinctly higher than for rPDGF-AA (cf. FIG. 4).

Figure 6:
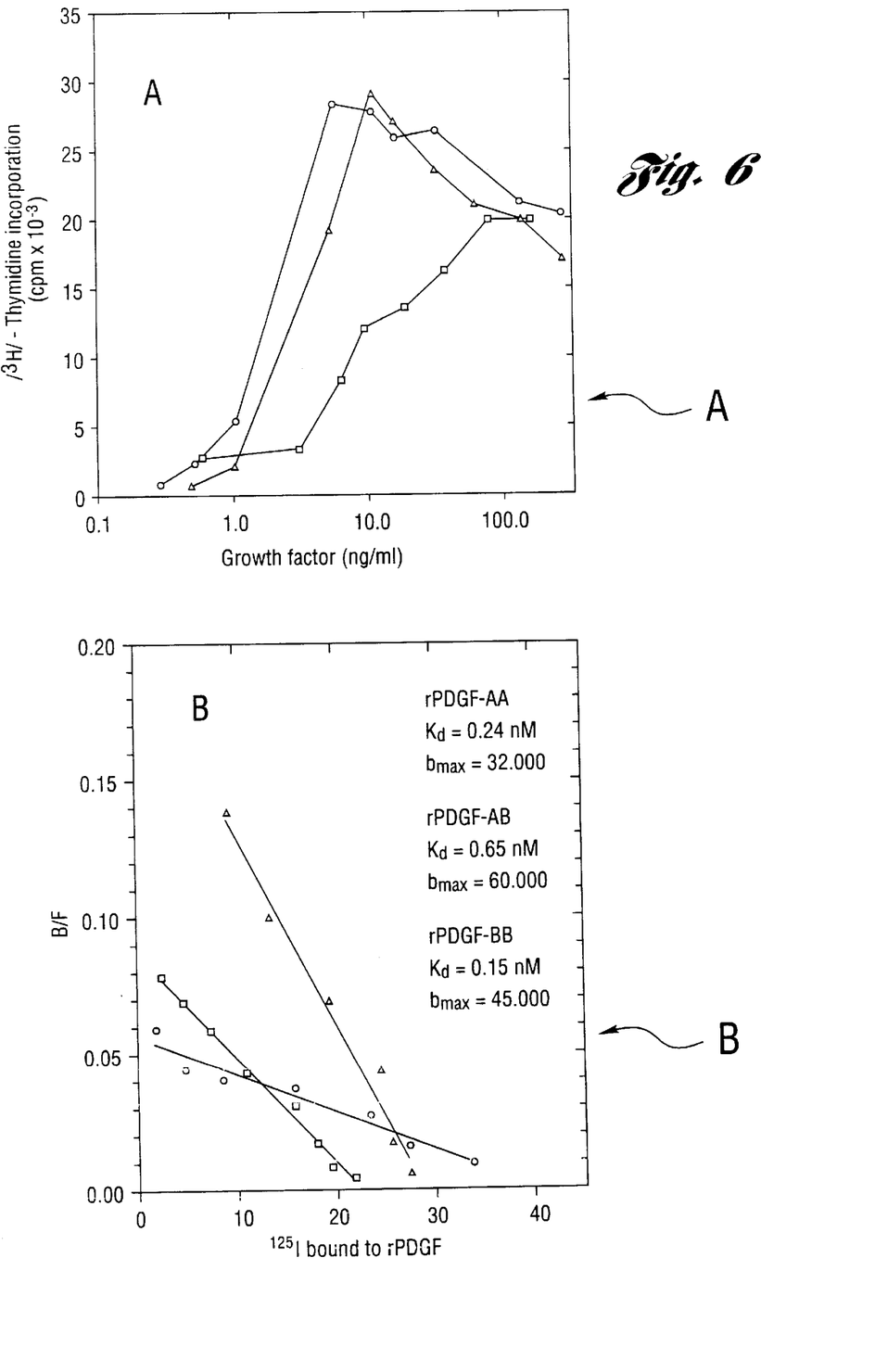

The biological activity of rPDGF-AB is comparable with that of human platelet PDGF and rPDGF-BB from *E. coli* (cf. FIG. 6).

Table 1

Amino-acid Analysis of rPDGF Isoforms

The figures in parentheses indicate the number of amino-acid residues produced from known sequences. Hydrolysis was carried out for 24 h; cysteine was determined as cysteic acid. No correction for degradation or incomplete hydrolysis was undertaken. The figures are means from four determinations.

| Amino acid | Amount in rPDGF-AA mol/mol | rpDGF-BB | rPDGF-AB |
|---|---|---|---|
| Asp | 14 (14) | 16 (16) | 15.0 (15) |
| Thr | 14.3 (16) | 14.7 (16) | 14.9 (16) |
| Ser | 14.3 (16) | 6.1 (6) | 10.9 (11) |
| Glu | 27.3 (28) | 24.6 (24) | 26 (26) |
| Pro | 16.7 (16) | 12.3 (14) | 15.4 (14) |
| Gly | 3.1 (2) | 3.5 (2) | 4.1 (2) |
| Ala | 12.1 (12) | 14.6 (14) | 13.1 (13) |
| Cys | 15.5 (16) | 16.3 (16) | 13.1 (16) |
| Val | 27.3 (30) | 19.6 (24) | 25.0 (27) |
| Ile | 8.2 (8) | 10.4 (12) | 9.3 (10) |
| Leu | 10.6 (10) | 11.9 (12) | 10.9 (11) |
| Tyr | 4.4 (6) | 0.3 (0) | 2.1 (3) |
| Phe | 1.9 (2) | 5.4 (6) | 3.3 (4) |
| Lys | 17.2 (18) | 12.7 (14) | 15.0 (16) |
| His | 5.4 (6) | 1.9 (2) | 3.7 (4) |
| Arg | 16.8 (18) | 20.7 (24) | 19.1 (21) |

TABLE 2

NH$_2$-terminus sequence analyses of rPDGF-AB
20 µg of rPDGF-AB were used for gas/liquid sequencing

| Cycle | Amino acid found | | Sequence at the NH$_2$ terminus | |
|---|---|---|---|---|
| | (pmol) | | A chain | B chain |
| 1 | S | I | S | I |
| 2 | I | A | I | A |
| 3 | E | E | E | E |
| 4 | E | — | E | C |
| 5 | A | K | A | K |
| 6 | Y (165) | T (195) | V | T |
| 7 | P (193) | R (98) | P | R |
| 8 | A (220) | T (210) | A | T |
| 9 | V (88) | E (150) | Y | E |
| 10 | — | V | C | V |

We claim:

1. PDGF-AB, which can be prepared by
   (I) expressing in *Escherichia coli*, a β-galactosidase/PDGF-A fusion protein wherein the PDGF-A has the amino acid sequence of SEQ ID NO: 1;
   (II) reducing the expressed fusion protein;
   (III) chemically cleaving the reduced fusion protein, if appropriate whereby the monomer containing thiol groups is liberated;
   (IV) sulfonating the thiol groups of the liberated monomer and of a second monomer to protect the thiol groups, the second monomer being selected from the group consisting of:
       (a) PDGF-B of SEQ ID NO: 2; and
       (b) PDGF-B of SEQ ID NO: 3;
   (V) purifying the protected monomers by chromatography in the presence of a denaturing agent;
   (VI) deprotecting the protected groups;
   (VII) dimerizing the deprotected monomers in the presence of reagents selected from the group consisting of urea and thiol reagents; and
   (VIII) purifying the dimer.

2. PDGF-AB, which can be prepared by
   (I) expressing in *Escherichia coli*, a β-galactosidase/PDGF-A fusion protein wherein the PDGF-A has the amino acid sequence of SEQ ID NO: 1;
   (II) reducing the expressed fusion protein;
   (III) chemically cleaving the reduced fusion protein, if appropriate whereby the monomer containing thiol groups is liberated;
   (IV) sulfonating the thiol groups of the liberated monomer and of a second monomer to protect the thiol groups, the second monomer being selected from the group consisting of:
       PDGF-B of SEQ ID NO: 3 in which the C-terminus is modified by the addition or deletion of up to 14 amino acids;
   (V) purifying the protected monomers by chromatography in the presence of a denaturing agent;
   (VI) deprotecting the protected groups;
   (VII) dimerizing the deprotected monomers in the presence of reagents selected from the group consisting of urea and thiol reagents; and
   (VIII) purifying the dimer.

3. A process for the preparation of PDGF-AB, which comprises:
   (I) providing *Escherichia coli*, containing a hybrid vector formed from pEX and foreign DNA which encodes a β-galactosidase/PDGF-A fusion protein wherein the PDGF-A has the amino acid sequence of SEQ ID NO: 1;
   (II) reducing the expressed fusion protein;
   (III) chemically cleaving the reduced fusion protein, if appropriate, whereby the monomer containing thiol groups is liberated;
   (IV) sulfonating the thiol groups of the liberated monomer and of a second monomer to protect the thiol groups, the second monomer being selected from the group consisting of:
       (a) PDGF-B of the amino acid sequence SEQ ID NO: 2; and
       (b) PDGF-B of the amino acid sequence SEQ ID NO: 3;
   (V) purifying the protected monomers by chromatography in the presence of a denaturing agent;
   (VI) deprotecting the protected groups;
   (VII) dimerizing the deprotected monomers in the presence of reagents selected from the group consisting of urea and thiol reagents; and
   (VIII) purifying the dimer.

4. A process according to claim 3, wherein the hybrid vector is formed by using pEX, selected from the group consisting of pEX1, pEX2 and pEX3.

5. A process for the preparation of PDGF-AB, which comprises:
   (I) providing *Escherichia coli*, containing a hybrid vector formed from pEX and foreign DNA which encodes a β-galactosidase/PDGF-A fusion protein wherein the PDGF-A has the amino acid sequence of SEQ ID NO: 1;
   (II) reducing the expressed fusion protein;
   (III) chemically cleaving the reduced fusion protein, if appropriate, whereby the monomer containing thiol groups is liberated;
   (IV) sulfonating the thiol groups of the liberated monomer and of a second monomer to protect the thiol groups, the second monomer being selected from the group consisting of:
       PDGF-B of SEQ ID NO: 3 in which the C-terminus is modified by the addition or deletion of up to 14 amino acids;
   (V) purifying the protected monomers by chromatography in the presence of a denaturing agent;
   (VI) deprotecting the protected groups;
   (VII) dimerizing the deprotected monomers in the presence of reagents selected from the group consisting of urea and thiol reagents; and
   (VIII) purifying the dimer.

6. A process according to claim 5, wherein the hybrid vector is formed by using pEX, selected from the group consisting of pEX1, pEX2 and pEX3.

7. A process according to claim 5, wherein cyanogen bromide is used for chemically cleaving.

8. A process according to claim 5, wherein sulfonation is carried out in the presence of sulfite and dithionate.

9. A process according to claim 5, wherein the purification is carried out by chromatography selected from the group consisting of gel permeation chromatography and reverse phase chromatography.

10. A process according to claim 5, wherein gel permeation chromatography is used and carried out in the presence of guanidine hydrochloride as the denaturing agent.

11. A process according to claim 5, wherein dimerization is carried out in the presence of urea and a thiol reagent selected from the group consisting of 2-mercaptoethanol, glutathione, dithiothreitol and dithioerythritol.

12. A process according to claim 5, wherein the chromatography in steps (V) and (VIII) is selected from the group consisting of reverse phase chromatography and ion exchange chromatography.

* * * * *